US006622562B2

(12) United States Patent
Angelsen et al.

(10) Patent No.: US 6,622,562 B2
(45) Date of Patent: Sep. 23, 2003

(54) MULTI PRE-FOCUSED ANNULAR ARRAY FOR HIGH RESOLUTION ULTRASOUND IMAGING

(76) Inventors: Bjorn A. J. Angelsen, Bugges veg 4b 7051, Trondheim (NO); Tonni F. Johansen, Osloveien 6 7018, Trondheim (NO)

( * ) Notice: Subject to any disclaimer, the term of this patent is extended or adjusted under 35 U.S.C. 154(b) by 19 days.

(21) Appl. No.: 10/041,309

(22) Filed: Jan. 7, 2002

(65) Prior Publication Data

US 2002/0139193 A1 Oct. 3, 2002

Related U.S. Application Data

(60) Provisional application No. 60/259,887, filed on Jan. 5, 2001.

(51) Int. Cl.[7] ........................ C01N 9/24; A61B 8/12; G01S 15/00

(52) U.S. Cl. ........................ 73/633; 73/626; 73/641; 600/447; 367/103

(58) Field of Search ........................ 73/633, 609, 610, 73/612, 626, 628, 641, 632, 618, 619, 620, 625, 642; 600/444, 447; 367/103, 105, 199

(56) References Cited

U.S. PATENT DOCUMENTS

| | | | | | |
|---|---|---|---|---|---|
| 4,569,231 | A | * | 2/1986 | Carnes et al. | 73/626 |
| 4,580,451 | A | * | 4/1986 | Miwa et al. | 73/626 |
| 4,662,223 | A | * | 5/1987 | Riley et al. | 73/626 |
| 4,670,683 | A | * | 6/1987 | 't Hoen | 310/334 |
| 4,694,434 | A | * | 9/1987 | von Ramm et al. | 367/7 |
| 5,027,659 | A | * | 7/1991 | Bele et al. | 73/626 |
| 5,127,410 | A | * | 7/1992 | King et al. | 600/459 |
| 5,490,512 | A | * | 2/1996 | Kwon et al. | 600/447 |
| 5,562,906 | A | * | 10/1996 | Terry et al. | 424/771 |
| 5,911,221 | A | * | 6/1999 | Teo | 600/447 |
| 5,922,962 | A | | 7/1999 | Ishrak et al. | 73/632 |
| 5,980,458 | A | * | 11/1999 | Clark | 600/437 |
| 6,014,897 | A | * | 1/2000 | Mo | 73/628 |
| 6,193,659 | B1 | * | 2/2001 | Ramamurthy et al. | 600/443 |
| 6,419,633 | B1 | * | 7/2002 | Robinson et al. | 600/443 |

* cited by examiner

*Primary Examiner*—Hezron Williams
*Assistant Examiner*—Jacques Saint-Surin
(74) *Attorney, Agent, or Firm*—Cohen, Pontani, Lieberman & Pavane

(57) ABSTRACT

An annular ultrasound bulk wave transducer array for electronic depth steering of symmetric focus from a near focus $F_n$ to a far focus $F_f$ includes elements that are divided into k groups with different fixed prefocusing. The central group participates in beam forming from $F_n$ to $F_f$, the next outer group in beam forming from $F_{n1}>F_n$ to $F_f$, and the kth outer group in beam forming from $F_{nk}>F_{n,k-1}$ to $F_f$. The fixed focus for the kth group is selected at $F_k$ between $F_{nk}$ and $F_f$. In this manner, beam formation close to $F_n$ is performed only by the central group. By steering the focus outward from $F_n$, the focal diameter increases and, at a depth where the focal diameter exceeds a limit, the next outer group of elements is included in beam formation. This increase in aperture area reduces the focal diameter with subsequent increases in diameter as the focus is further steered toward $F_f$. In the same manner, the kth group of elements is included in beam formation for steered foci deeper than $F_{nk}$, presenting a growing aperture that enables maintenance of the diameter below limits with a low total number of elements and avoids impractically small widths of the annular elements. The elements may also be subdivided in the angular direction, allowing for phase aberration correction.

8 Claims, 9 Drawing Sheets

MULTI PRE-FOCUSED ANNULAR ARRAY FOR HIGH RESOLUTION ULTRASOUND IMAGING

This application claims the benefit of a Provisional Application No. 60/259,887 filed Jan. 5, 2001.

BACKGROUND OF THE INVENTION

1. Field of the Invention

The present invention is directed to technology and design of ultrasound transducer arrays with symmetric electronic steering of the focus for ultrasound imaging, particularly both two-dimensional and three-dimensional medical ultrasound imaging.

2. Description of the Related Art

Ultrasound array transducers are used in ultrasound imaging for electronic direction steering and focusing of the ultrasound beam. The commonly used arrays have a linear arrangement of the elements for two-dimensional scanning of the beam. The linear phased arrays, for example, produce a sector scanning of the beam centered at the array, while the linear or curvilinear switched arrays provides a wider image field at the transducer.

A problem with the linear arrangement of the elements, is that the beam focus can be electronically steered only within the two-dimensional (2D) scan plane, what is referred to as the azimuth direction. The beam focus in the direction normal to the 2D scan plane, what is referred to as the elevation direction, must with these arrays be set to a fixed depth.

In many practical situations one makes a 2D ultrasound image where the variation of the object is limited transverse to the 2D scan plane (i.e. in the elevation direction). Such examples are short and long axis imaging of the heart, imaging of the fetal trunk and head, amongst other. In such cases there is limited need for electronic steering of the elevation focus. On the other hand, imaging of objects with short dimension in the elevation direction, like vessels, cysts, a fetal heart, etc., is greatly improved when the beam has an electronically steered focus both in the elevation and the azimuth directions. Electronic steering of both the elevation and azimuth focus is also important for three-dimensional (3D) imaging where the object can be viewed from any perspective (direction) that favors optimal focusing with minimal resolution in all directions.

Electronic steering of the focus in the elevation direction can be obtained by dividing the linear array elements into sub elements in the elevation direction. A particular solution to such steering of the elevation focus is given in U.S. Pat. No. 5,922,962. However, to obtain full symmetric steering of the azimuth and elevation foci, a large number of elements is required with this solution, complicating the cabling and drive electronics for this array. Also, the elements of this array becomes small, increasing the electrical impedance of the elements that increases noise and cable losses, which further limits the maximal frequency that can be used with such arrays for a given depth, and consequently the resolution obtainable with these arrays at a given depth.

Another, well known method to obtain an electronically steered symmetric focus is to use an array of concentric annular elements, the so-called annular array. Such an array is usually pre-focused mechanically to a depth F, either by curving the array or by a lens, or by a combination of the two. The focus, F, is then steered electronically from a near focus $F_n<F$ to a far focus $F_f>F$ by adding delays to the element signals before they are added, according to well known principles. The beam will then be optimally focused symmetrically around the beam axis, i.e. equally focused in the azimuth and the elevation directions, with fewer and larger elements than with the 2D arrays described above. This gives lower electric impedance of the elements, reducing noise and cable losses with improved sensitivity compared to the 2D arrays. For mechanical scanning of the beam direction, the annular array is immersed in a fluid inside a dome. The array itself is therefore not pushed against the skin as the linear arrays, and can hence be made with a lighter weight backing than the linear arrays, for example a plastic foam. This reduces the backing losses which further improves the sensitivity of the annular arrays above the linear 2D arrays. The improved sensitivity of the annular array hence allows the use of higher ultrasound frequencies, which further improves the image resolution above the linear 2D arrays.

The fewer number of elements of the annular array compared to the 2D array, allows the use of wider apertures, which further reduces the focal diameter, and hence improves the lateral resolution. With very wide aperture annular arrays, however, the outer elements can become quite narrow when steering of the focus over a large range is required. This can introduce complex vibration modes of the elements, reducing the efficiency of the elements. Further, narrow elements complicate the manufacturing and increase the total number of elements in the array which complicates electrical connections to the moving array.

The present invention presents a solution to this problem with annular arrays by acoustically pre-focusing the annular elements at different depths, where a core group of elements are pre-focused to participate in the active aperture for the whole image range. Outer elements that are pre-focused at deeper ranges are then included to the active aperture at deeper ranges so that the angular expansion of the focal diameter with depth is reduced by the increased aperture size. The invention hence allows the full use of the advantages of the annular arrays: 1) A symmetrical focus that is steered electronically within the actual image range, 2) fewer and larger elements with the annular array with lower impedance backing gives high sensitivity that allows for the use of high frequencies with improved resolution, and 3) the lower number of elements simplifies the front end electronics.

Objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the various Figures:

FIG. 1 shows an example annular array where

FIG. 2 shows an illustration to calculation of the phase error across the elements from a point source in the steered focus, where FIG. 2*a* illustrates calculations for a plane array, while

FIG. 3 illustrates a method of selecting the pre-focuses of the elements to obtain an expanding aperture that limits angular expansion of the steered focus with depth while using maximal width of the elements, where

DETAILED DESCRIPTION OF THE PRESENTLY PREFERRED EMBODIMENTS

A particular embodiment of the invention will be explained with reference to the Figures.

Figure 1A:
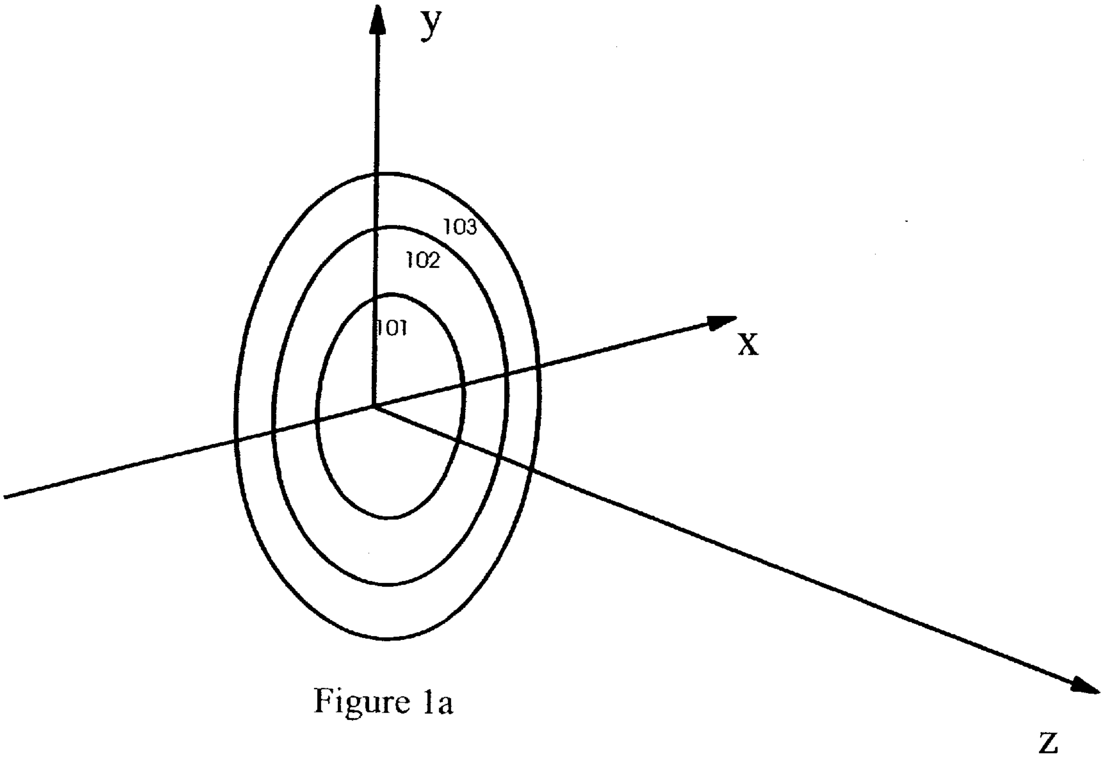
FIG. 1*a* shows a front view of the array with depiction of the radiating surface and coordinate system for the description.
Figure 1B:
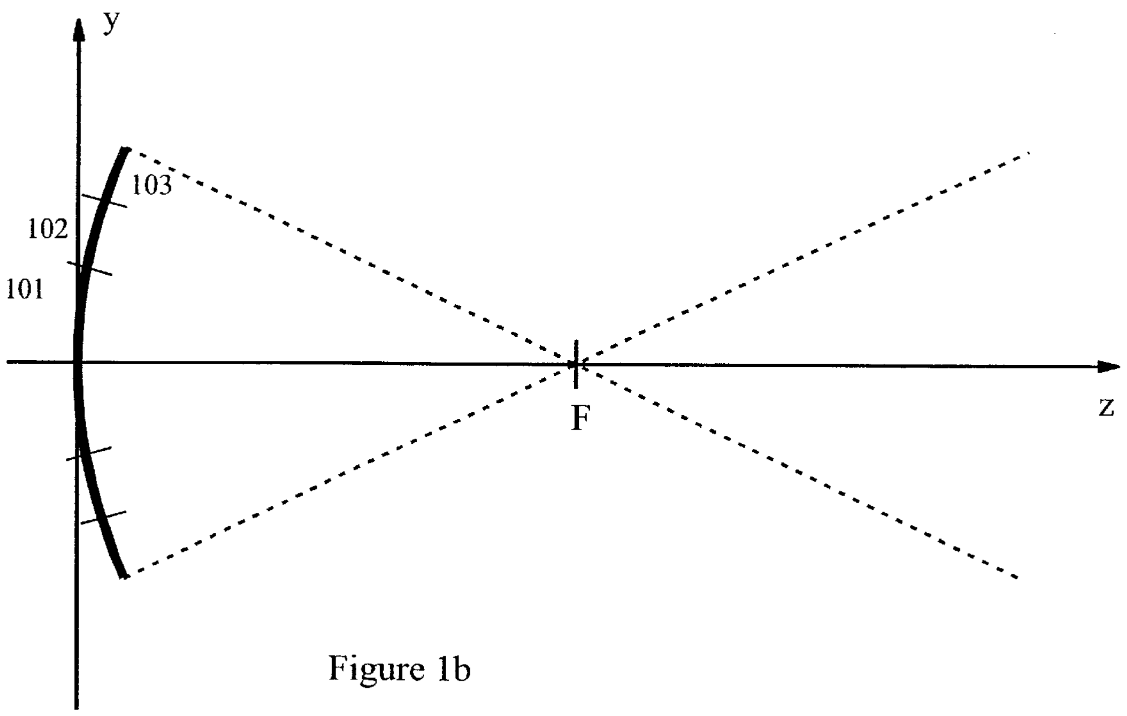
FIG. 1*b* shows a side view that illustrates a curved focusing of the array.

FIG. 1*a* shows a schematic front view of an example of a typical prior art annular array, where the coordinate x denotes the azimuth direction which is the 2D scan plane direction, the coordinate y denotes the elevation direction, and the coordinate z denotes the depth. In this example, the elements are composed of a center disc 101 with two concentric annuli 102 and 103. By shaping the array as a spherical shell with center at a depth F, the array is pre-focused to this depth, as illustrated in FIG. 1*b*. A lens of a material with acoustic velocity different from that of the load material, can also be used for the pre-focusing.

Figure 2A:
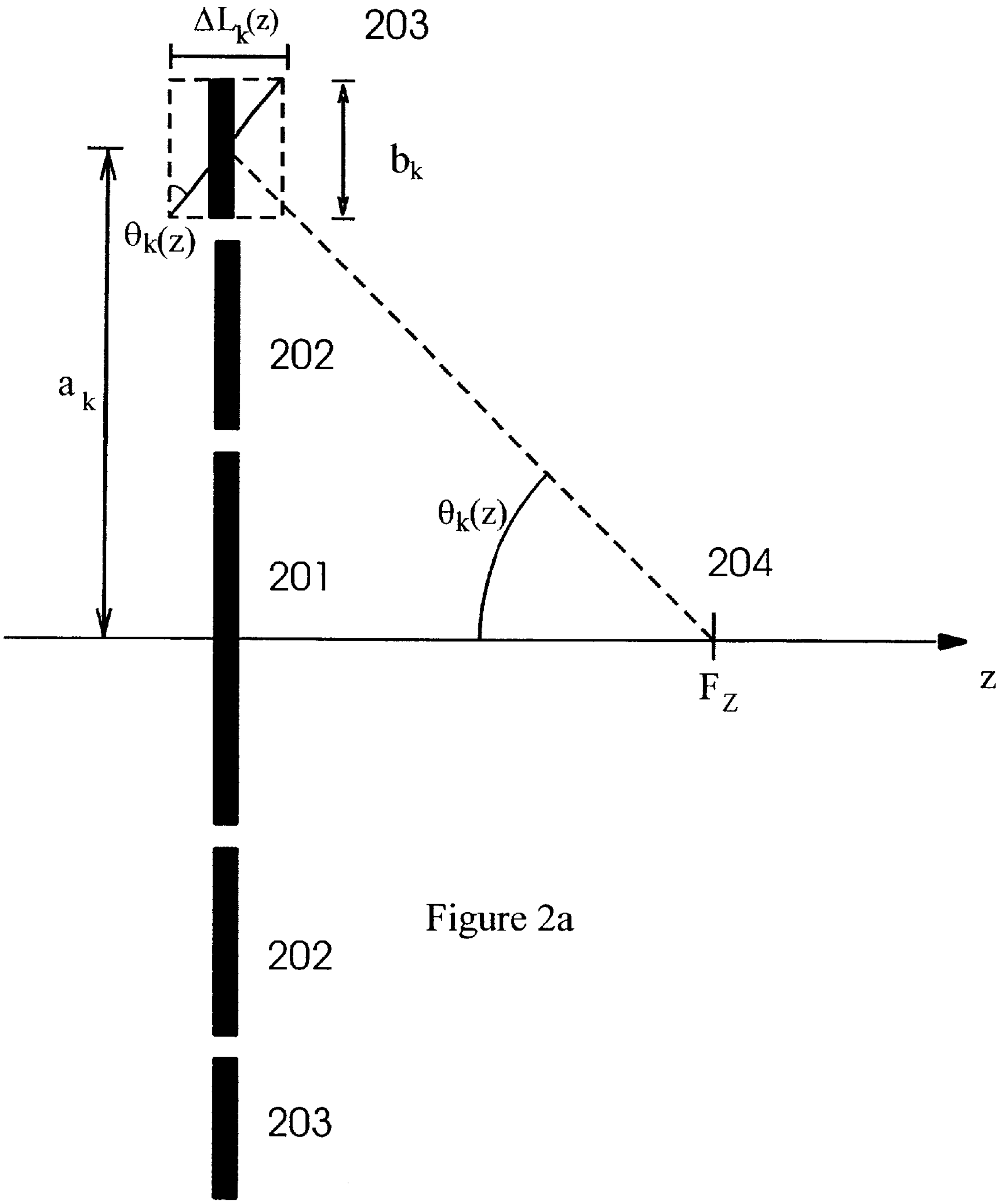

FIG. 2*a* shows a a cross section in the elevation direction of plane annular array, depicting the cross section of a set of elements 201, 202, and 203. A requirement for adequate participation of an element in the formation of a focused aperture, is that the phase error across the element of a spherical wave from a point source in the steered focus, is less than a certain limit, typically ~$\alpha\pi/2$, where $\alpha$~1. The degradation of the beam with increasing phase error is continuous, so that there is not a sharp limit on the acceptable value of $\alpha$, where $\alpha$=1.5 can in many cases be tolerable. For the steered focus $F_z$ at 204 in FIG. 2*a* we see that the phase error $\Delta\phi_k(z)$ across element #k is, when approximating the wave front over the element by a plane wave (plane wave approximation)

$$\Delta L_k(z) = \frac{b_k a_k}{F_z} \tag{1}$$

$$\Delta\phi_k(z) = 2\pi\frac{\Delta L_k(z)}{\lambda} = 2\pi\frac{b_k a_k}{\lambda F_z}$$

where $\lambda$ is the ultrasound wave length, $a_k$ is the radius of the element center, and $b_k$ is the element width. We hence see that as the radius $a_k$ of the element center increases, the element width $b_k$ must be reduced to maintain the phase error below the acceptable limit. We note that for the area for rings is $2\pi a_k b_k$ which implies that the phase error is the same with equal area elements. We also note that as the steered focus $F_z$ is reduced, the phase error increases, which limits the maximal $a_k$ to be used at low ranges with a given $b_k$.

Figure 2B:
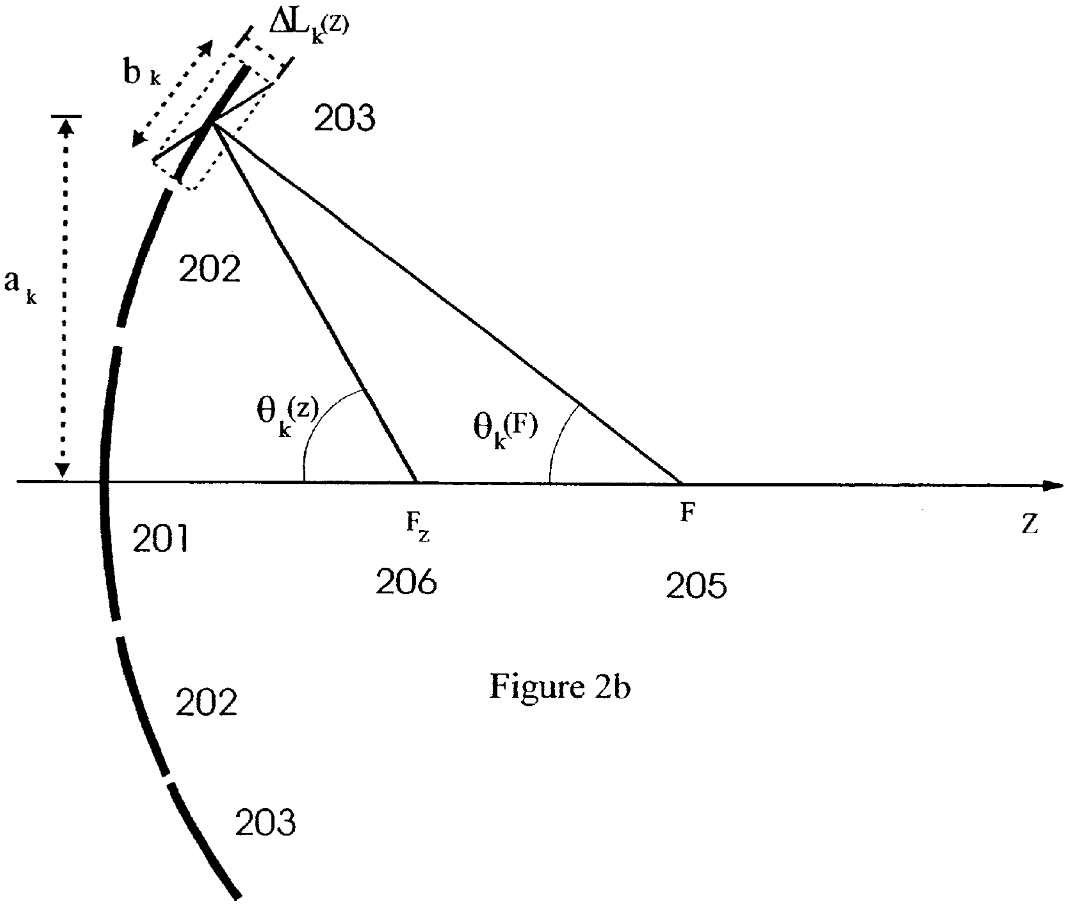
FIG. 2*b* illustrates calculations for a focused array.
Figure 3A:
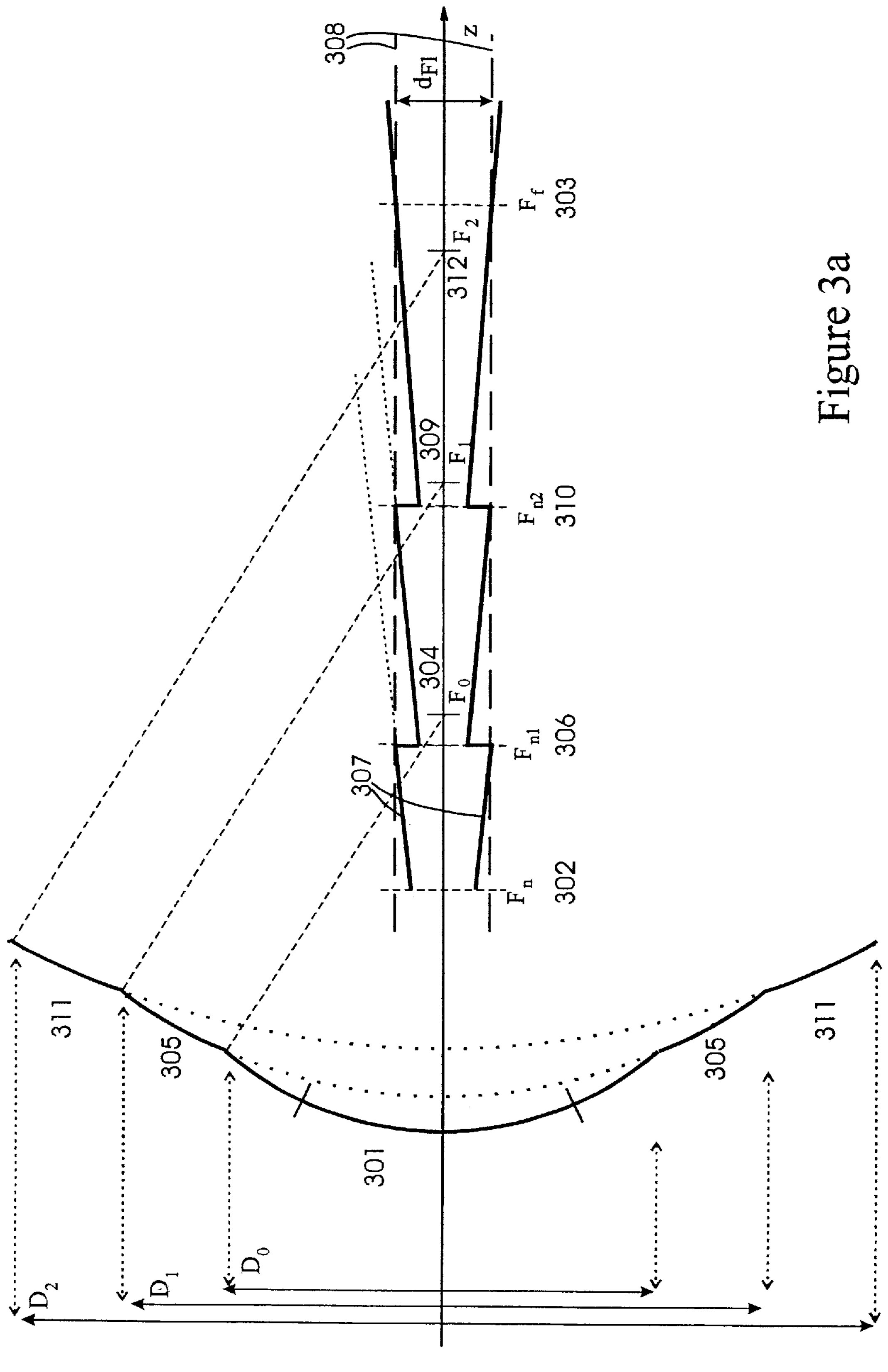
FIG. 3*a* illustrates the basic principles with pre-focusing obtained by curving of the elements.
Figure 3B:
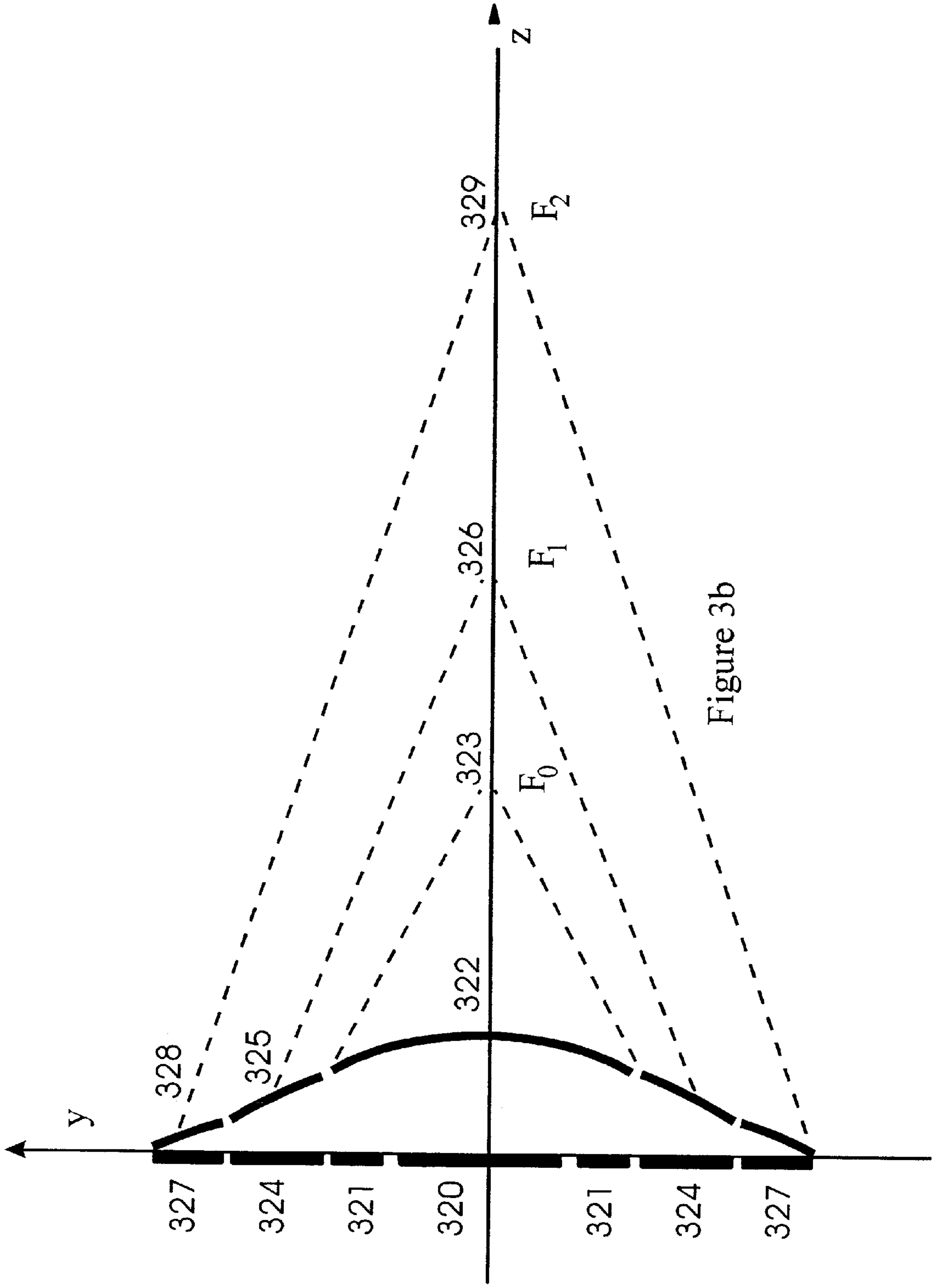
FIG. 3*b* illustrates pre-focusing obtained by lenses.

To be able to increase the width of the elements while the phase error is less than a limit, the array can be pre-focused to a depth F, either by curving of the array as a spherical shell with center at F at 205 in FIG. 2*b*, or using a lens as shown in FIG. 3*b*, or a combination of both. Which of these methods that are preferred, depend on the actual situation.

The phase error across each element is then zero for waves originating from the fixed focus F, and increases as the steered focus $F_z$ at 206 in FIG. 2*b* is moved inwards or outwards from F. With reference to FIG. 2*b* we see that the phase error in this case can in the plane wave approximation be obtained as $$\Delta\phi_k(z) = \frac{2\pi}{\lambda}\left(\frac{1}{F_z} - \frac{1}{F}\right)b_k a_k \tag{2}$$

We see that also for this array with constant curvature, equal area elements gives the same phase error across each element. We also note that for a given $b_k$ one must reduce the aperture (i.e. maximal $a_k$) as $F_z$ is both increased or reduced from F to maintain $\Delta\phi_k(z)$ below acceptable limits.

The diameter of the beam focus, can be expressed as $$d_F(z) = 2\frac{\lambda}{D_k}F_z \tag{3}$$

where $D_k=2a_k+b_k=d_k+b_k$ is the diameter of the active aperture with k elements electronical focused at the depth $F_z$. As the field has a smooth drop in amplitude from the axial value, Eq.(3) is only an approximate assessment of the focal diameter. It corresponds for the circular aperture with uniform excitation to approximately 12 dB drop of the field amplitude from the axial value. We note that $d_F(z)$~$F_z$, which implies that for fixed active aperture diameter $D_k$ the beam has a fixed angular expansion with depth. One hence wants to increase the active aperture with depth to avoid that the focal diameter expands without limit, for example by increasing the number of participating elements with depth. With the same fixed focus of all participating elements, this requires that $b_k$ is reduced with increasing k proportional to $1/a_k$ to satisfy a limit on $\Delta\phi_k(Z)$ in Eq.(2), which makes the outer elements very narrow and increases the number of elements.

The invention provides a solution to this problem by dividing the annular elements into groups of neighboring elements, where each group has a different pre-focus obtained by mechanical curving of the elements, or a lens, or a combination of both. The depth of a group's pre-focus increases with the group's distance from the array center. An example of such an embodiment of the invention is given in FIG. 3*a*. In this particular embodiment, a central group of elements 301 with total aperture diameter $D_0$ participates in the active aperture over the whole steered focusing range of the array, i.e. from a steered near focus $F_n$ at 302 to a steered far focus $F_f$ at 303. This group of elements has a common pre-focus $F_0$ at 304, preferably selected so that the phase error is the same at the far focus $F_f$ and the near focus $F_n$. With the plane wave approximation, this gives a pre-focus $$F_0 = \frac{2F_n F_f}{F_n + F_f} \tag{4}$$

This pre-focus also gives the minimal phase error for the participating elements over the whole focusing range. Reducing the width of the elements as $b_k$~$1/a_k$, the area $A_k=2\pi a_k b_k$ of the annular elements are independent of $a_k$. Hence, equal area annular elements gives the same phase error for all elements in the group, and as the area is constant, the electric impedance is similar for all the elements in the group.

The focus $F_z$ is steered electronically outwards from $F_n$ by adding delays to the signals of the individual elements in the group according to well known methods. The focal diameter increases with $F_z$ according to Eq.(3) with $D_k=D_0$, and indicated by the lines 307 in FIG. 3*a*. When the focal diameter exceeds a selected limit $d_{F1}$ indicated by the lines 308, a new group of elements 305 is added to the active aperture at a depth $F_{n1}$ at 306. The new group of elements participates in the active aperture from $F_{n1}$ to $F_f$, and is given a pre-focus $F_1$ at 309 in this range, preferably so that the phase error across each element is minimized for $F_z$ in the range from $F_{n1}$ to $F_f$. With the plane wave approximation, this gives a fixed focus of $$F_1 = \frac{2F_{n1}F_f}{F_{n1}+F_f} \tag{5}$$

This increase in active aperture diameter to $D_1$ produces a reduction in the focal diameter below the limit $d_{F1}$, as indicated by the lines 307 that describes Eq.(3).

The focus $F_z$ is furthered steered electronically outwards from $F_{n1}$ by adding delays to the signals for all the elements that participates in the apertures, and the focal diameter further increases with $F_z$ according to Eq.(3) with the new active aperture diameter $D_k=D_1$. At a depth $F_{n2}$ at 310 the focal diameter again passes a selected limit $d_{F1}$ where the procedure is repeated so that a new group of elements 311 is added to the active aperture so that one gets a diameter of the active aperture of $D_2$ for $F_z>F_{n2}$. The new element group 311 is pre-focused to a depth $F_2$ at 312, preferably so that the phase error across these elements is minimized over the whole range of the steered focus from $F_{n2}$ to $F_f$ where the element group 311 participates in the active aperture.

Hence, the general procedure can be summarized so that for a given active aperture diameter $D_{m-1}$, the focal diameter increases with the focal depth according to Eq.(3) with $D_k=D_{m-1}$, and at the depth $F_{nm}$ where the focal diameter exceeds a selected limit $d_{F1}$, the aperture is increased with a new group of elements to participate in the active aperture from $F_{nm}$ to $F_f$, and pre-focused in this range, preferably so that the phase error across the new elements are minimized for the steered focus in the whole range $F_{nm}$ to $F_f$ where the new group participates in the active aperture. The pre-focus is then with the plane wave approximation for the phase error, given as $$F_m = \frac{2F_{nm}F_f}{F_{nm}+F_f} \tag{6}$$

The advantage of the multiple pre-focusing of groups of elements compared to a fixed pre-focus annular array, is that one can use larger area of the elements as the pre-focus is increased, because the elements participates to the active aperture for a shorter range. This reduces the total number of elements and hinders that the element width $b_k$ becomes impractically narrow. The net result is hence a practical way to obtain so wide active aperture for the deep ranges that a low diameter of the steered focus is maintained as the focal depth increases.

We have in this description used a fixed limit $d_{F1}$ of the focal diameter, where the active aperture is expanded with new elements. It is clear that in the general spirit of the invention, this limit can vary, say $d_{F1}=d_{Fm}$ to satisfy other design requirements, like a weakly expanding maximal focus to reduce the total number of elements.

The procedure above is then applied for expanding the aperture with one or more new annular elements when the focal diameter increases above a selected limit $d_{Fm}$. The pre-focus of the new elements is preferably chosen as in Eq.(6), and the width of the elements are chosen so that the phase error across the elements is kept below a limit (e.g. $\alpha\pi/2$ where $\alpha\sim1$) for the steered focus at the outer limits, i.e. at $F_{nm}$ and $F_f$. We then recall that equal area of the elements in the group gives the same phase error across each element, and also the same electrical impedance for the elements. It is also convenient to use element areas for each new group that are a whole number multiplied by the area of the elements in the first group. This makes a simple solution for matching of the transmitter and receiver amplifiers to the different element impedances in each group, by parallel coupling a number of equal transmitter and receiver amplifiers to each element, given by the fraction of the element area to the area of the central elements.

The pre-focusing of the elements can be obtained by individual curving of the array elements, as shown in FIG. 3*a*, or by a multiple focused lens system as in FIG. 3*b*. This Figure shows a plane annular array where the elements 320, 321 participate in the active aperture from $F_n$ to $F_f$ and are pre-focused with the lens 322 to a depth $F_0$ at 323, while the element 324 participates in the active aperture from $F_{n1}$ to $F_f$ and is pre-focused by the lens 325 to a depth $F_1$ at 326, and the element 327 participates in the active aperture from $F_{n2}$ to $F_f$ and is pre-focused by the lens 328 to a depth $F_2$ at 329.

Figure 3C:
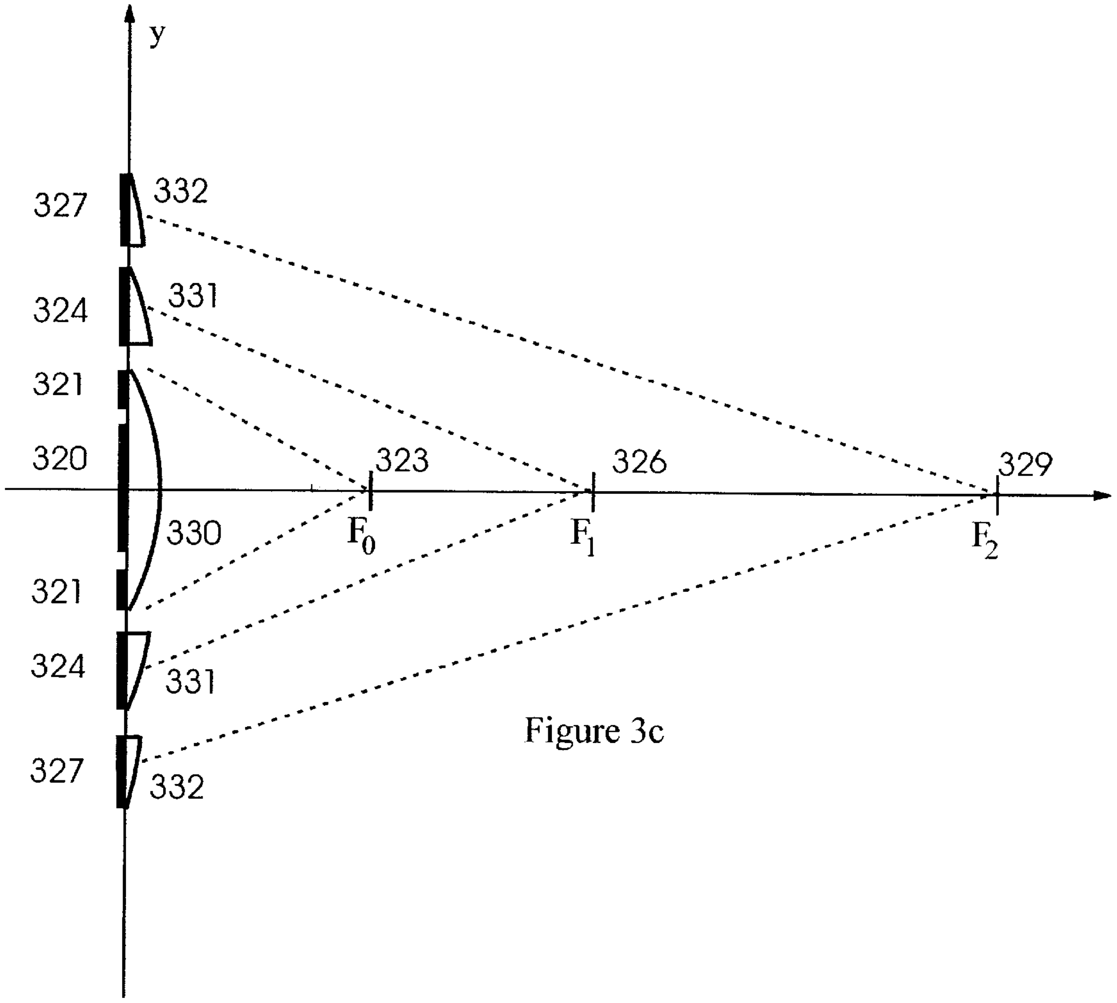
FIG. 3*c* illustrates pre-focusing obtained by thin lenses.
Figure 3D:
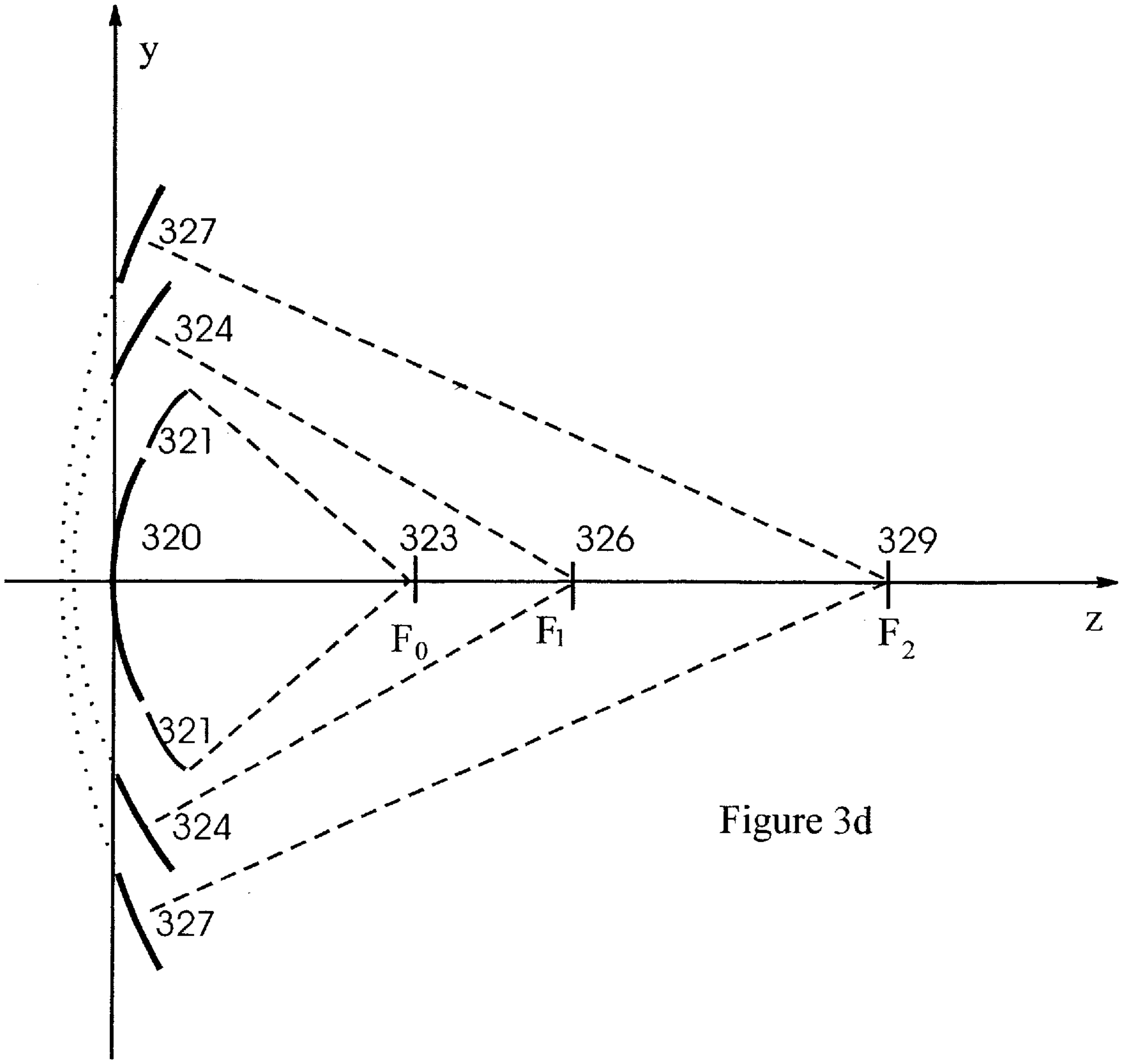
FIG. 3*d* illustrates pre-focusing by curved elements with offset positions.

Due to absorption and pulse reverberations in the lens, it is advantageous to make the lens as thin as possible. This is achieved by the lens system 330, 331, 332 of FIG. 3*c* which provides the same reduction in phase error across the elements as the lens system 322, 325, 328 of FIG. 3*b*. The important function of the lens or curving of the elements, is to minimize the phase error across each element for the range of steered foci where the elements participate in the active aperture. One can then adjust the individual time delays of the element signals to compensate for reductions in lens thickness, or offset positioning of the elements as shown in FIG. 3*d*. The positioning of the elements as in FIG. 3*a* gives the simplest manufacturing of a curved array, although some offset positioning of the elements gives lower maximal delays of the element signals for focusing in the whole range from $F_n$ to $F_f$.

In practical imaging, spatial variations in the acoustic properties of the tissue, such as the wave propagation velocity, reduces the focusing capabilities of an array below that what is theoretically possible with the design above. This phenomenon is often referred to as phase front aberrations, and can be corrected for by dividing the whole array into smaller elements, and filtering the signals from each element before they are further delayed and processed according to standard beam forming techniques. An approximate filtering of the element signals are obtained by delay and amplitude corrections of the signals.

Figure 4:
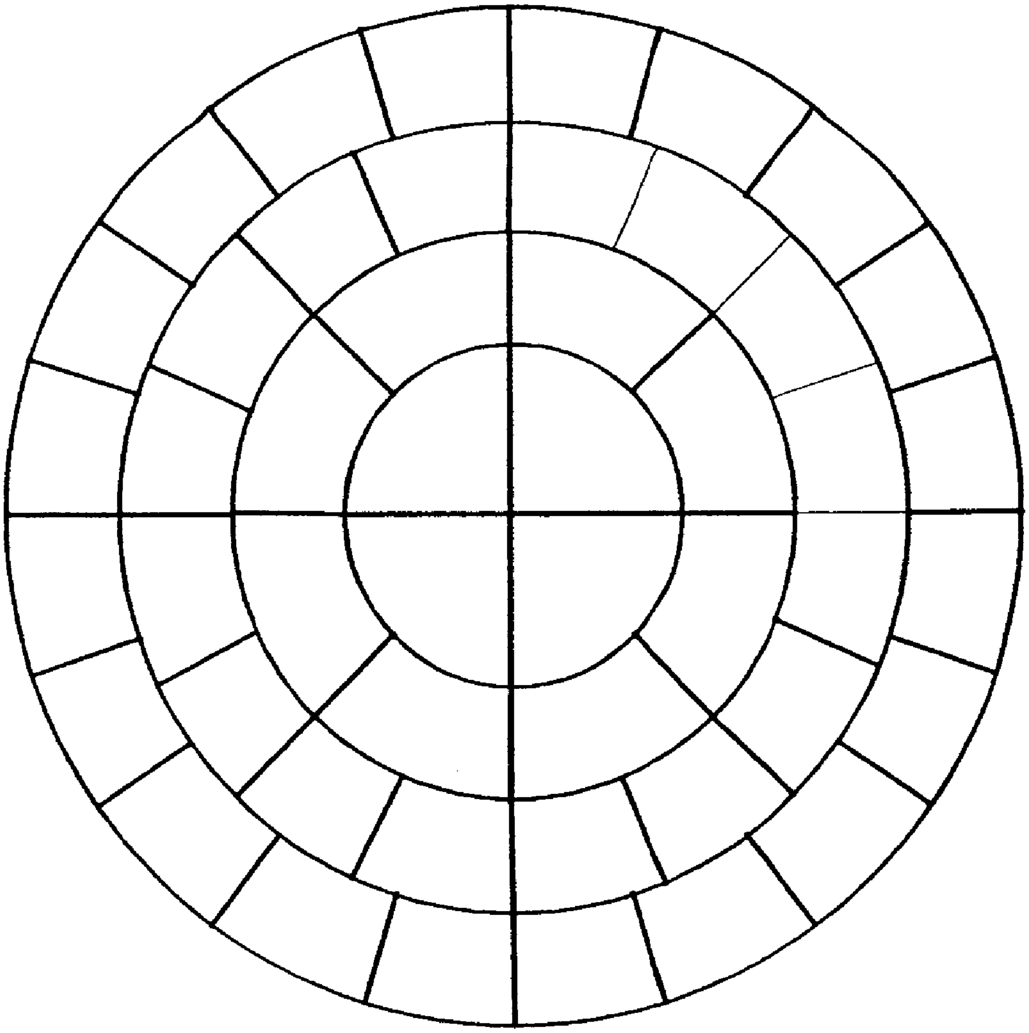
FIG. 4 illustrates how the same principle of multiple pre-focusing can be applied to an expanding aperture annular array with added angular division of the elements.

An example of an array that allows for such phase aberration correction, is the r-θ array shown in FIG. 4. To allow for larger elements and reduce the total number of elements it is then advantageous to use multiple pre-focusing of the elements, where all elements located at the same distance from the center, is typically given the same pre-focus.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An ultrasound annular array transducer for electronic steering of a symmetric focus $F_z$ from a near focus, $F_n$ to a far focus $F_f$ by adding delays to array element signals, comprising:

a plurality of annular array elements divided into groups of at least one of neighboring elements of the plural array elements, each group having a different fixed mechanical pre-focus, and the array elements within each group having substantially equal area, wherein a central group of the plural groups of array elements participates in an active aperture of said transducer for the whole focal range from $F_n$ to $F_f$ with a pre-focus $F_0$ selected between $F_n$ and $F_f$, wherein beyond a depth $F_{n1}$ at which a focal diameter of the central group expands past a selected limit, a next outer group of array elements is included in the active aperture from $F_{n1}$ to $F_f$, a fixed pre-focus $F_1$ of the next outer group being selected between $F_{n1}$ and $F_f$, and wherein beyond each depth $F_{nm}$ the focal diameter expands past selected limits and the next outer group of elements is included in the active aperture from $F_{nm}$ to $F_f$, a fixed pre-focus $F_m$ of the next outer group being selected between $F_{nm}$ and $F_f$, so that the focal diameter of the array transducer is kept below selected limits within the whole region from $F_n$ to $F_f$ as the focus of the annular array is steered electronically.

2. An ultrasound transducer array according to claim 1, wherein the pre-focus of each group of elements is selected so that a maximal phase error across each array element in the each group is minimized within a region in which the each group participates to the active aperture.

3. An ultrasound transducer array according to claim 1, wherein pre-focusing of the array elements is obtained by curving the array elements.

4. An ultrasound transducer array according to claim 1, wherein pre-focusing of the array elements is obtained by an acoustic lens assembly.

5. An ultrasound transducer array according to claim 1, wherein pre-focusing of the array elements is obtained by a combination of curving the array elements and an acoustic lens assembly.

6. An ultrasound transducer array according to claim 1, wherein the area of the array elements of each group is selected as a whole number times the area of the array elements of the central group, and wherein to match a variable impedance between the array elements of different groups a number of transmitter and receiver amplifiers are parallel coupled to each array element, said number of transmitter and receiver amplifiers being equal to a ratio of the area of said each array element to the area of the central group array elements.

7. An ultrasound transducer array according to claim 1, wherein the annular elements are further divided in an angular direction for individual processing of signals from each of the array elements for phase aberration corrections.

8. An ultrasound transducer array according to claim 7, wherein radial and angular widths of the array elements are selected to be as large as possible without exceeding a correlation length of aberrations of a reflected wavefront received from tissue toward which signals from the ultrasound transducer are operatively directed.

* * * * *